US008673863B2

(12) United States Patent
Wang et al.

(10) Patent No.: US 8,673,863 B2
(45) Date of Patent: *Mar. 18, 2014

(54) GLUTATHIONE-BASED DELIVERY SYSTEM

(75) Inventors: Ae-June Wang, Hsinchu (TW);
Chi-Heng Jian, Yilan County (TW);
Shyh-Dar Li, Miaoli County (TW);
Yi-Fong Lin, Taipei County (TW);
Shin-Jr Liu, Kaohsiung County (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

This patent is subject to a terminal disclaimer.

(21) Appl. No.: 13/287,480

(22) Filed: Nov. 2, 2011

(65) Prior Publication Data

US 2012/0046445 A1    Feb. 23, 2012

Related U.S. Application Data

(60) Division of application No. 12/244,563, filed on Oct. 2, 2008, now Pat. No. 8,067,380, which is a continuation-in-part of application No. 12/000,261, filed on Dec. 11, 2007, now Pat. No. 7,704,956, which is a continuation-in-part of application No. 11/303,934, filed on Dec. 19, 2005, now Pat. No. 7,446,096.

(30) Foreign Application Priority Data

Dec. 30, 2005    (TW) .............................. 94147661 A

(51) Int. Cl.
*A61K 38/06* (2006.01)
*A61K 31/355* (2006.01)
*A61K 49/12* (2006.01)

(52) U.S. Cl.
USPC ......... 514/21.9; 514/458; 424/1.21; 530/331; 977/773

(58) Field of Classification Search
None
See application file for complete search history.

(56) References Cited

U.S. PATENT DOCUMENTS

| | | | |
|---|---|---|---|
| 5,080,904 A | 1/1992 | Iga et al. | |
| 5,695,751 A | 12/1997 | Friedman et al. | |
| 6,627,732 B1 | 9/2003 | Sakon et al. | |
| 6,653,331 B2 | 11/2003 | Zhao et al. | |
| 7,446,096 B2 * | 11/2008 | Wang et al. | 514/1.1 |
| 7,700,564 B2 * | 4/2010 | Wang et al. | 514/21.9 |
| 7,704,956 B2 * | 4/2010 | Liang et al. | 514/18.4 |
| 8,067,380 B2 * | 11/2011 | Wang et al. | 514/21.9 |
| 2003/0109555 A1 | 6/2003 | Zhao et al. | |
| 2009/0123531 A1 | 5/2009 | Wang et al. | |

FOREIGN PATENT DOCUMENTS

| | | |
|---|---|---|
| EP | 1 072 608 A1 | 1/2001 |
| FR | 2 627 385 A | 8/1989 |
| JP | 63-2922 A | 1/1899 |
| JP | 8-34779 A | 2/1996 |
| JP | 2001-503396 A | 3/2001 |
| JP | 2001-523221 A | 11/2001 |
| JP | 2004-323486 A | 11/2004 |
| WO | WO 99/54346 A1 | 10/1999 |
| WO | WO 00/28977 A1 | 5/2000 |

OTHER PUBLICATIONS

Suntres, 1994, J. Pharm. Pharmacol, 46, 23-28.*
Inoue, 1996, Clinical and Diagnostic Laboratory Immunology, 3, 663-668.*
"Liposome carrier for liver disease treatment—contains N-higher acyl glutathione as base material", Derwent, XP002322756, abstract (Jan. 7, 1988).
[Retrieved from] http://www.merriam-webster.com/dictionary/endogenous, 2 pages, 2009 [retrieved on May 20, 2009].
Anuradha, et al, "Possible Mechanisms of Insulin Antinociception," Methods Find Exp Clin Pharmacol, 2004, vol. 26, No. 1, pp. 5-8.
Banks et al., "Passage of Peptides Across the Blood-Brain Barrier: Pathophysiological Perspectives," Life Sciences, vol. 59, No. 23, 1996, pp. 1923-1943.
Chinese Office Action for Copending Application No. 200610005869.0, dated Dec. 15, 2010.
Jurima-Romet et al., "Lung Uptake of Liposome-entrapped Glutathione After Intratracheal Administration," Journal of Pharmacy and Pharmacology, 1991, vol. 43, No. 1, pp. 6-10.
Kabanov, et al.,"Mechanishm of Radiational Ionic Graft Polymerization," Institute of Physical Chemistry, 1982, pp. 771-775.
Kannan et al., "Evidence for the Existence of a Sodium-dependent Glutathione (GSH) Transporter," The Journal of Biological Chemistry, Apr. 19, 1996, vol. 271, No. 16, pp. 9754-9758.
Kannan et al., "GSH transport in human cerebrovascular endothelial cells and human astrocytes: evidence for luminal localization of Na+-dependent GSH transport in HCEC," Brain Research, 2000, vol. 852, pp. 374-382.
Kannan et al., "GSH Transport in Immortalized Mouse Brain Endothelial Cells: Evidence for Apical Localization of a Sodium-Dependent GSH Transporter," Journal of Neurochemistry, 1999, vol. 73, No. 1, pp. 390-399.
Khan, et al, "Enhanced Analgesic Activity of Liposomised Met-enkephalin Analogue," Indian Journal of Biochemistry & Biophysics, Dec. 1981, vol. 18, pp. 440-441.
Kiwada et al., " Application of Synthetic Liposomes Based on Acyl Amino Acids or Acyl Peptides as Drug Carriers. I. Their Preparation and Transport of Glutathione into the Liver," Chemical and Pharmaceutical Bulletin, Jul. 7, 1987, vol. 35, No. 7, pp. 2935-2942.
Office Action, dated Nov. 30, 2010, for Japanese Application No. 2005-374896.
Sugiyama et al., "Kinetic and biochemical analysis of carrier-mediated efflux of drugs through the blood-brain and blood-cerebrospinal fluid barriers: importance in the drug delivery to the brain," Journal of Controlled Release, Nov. 1, 1999, vol. 62, No. 1-2, pp. 179-186.

(Continued)

*Primary Examiner* — Satyanarayana R Gudibande
(74) *Attorney, Agent, or Firm* — Birch, Stewart, Kolasch & Birch, LLP

(57) ABSTRACT

A delivery system is provided. The delivery system includes a carrier or an active compound and a glutathione or a glutathione derivative grafted thereon. The invention also provides a compound including a moiety comprising a vitamin E derivative or a phospholipid derivative, a polyethylene glycol (PEG) or a polyethylene glycol derivative bonded thereto, and a glutathione (GSH) or a glutathione derivative bonded to the polyethylene glycol or the polyethylene glycol derivative.

10 Claims, 6 Drawing Sheets

(56) References Cited

OTHER PUBLICATIONS

Suntres et al., "Incorporation of α-Tocopherol in Liposomes Promotes the Retention of Liposome-encapsulated Glutathione in the Rat Lung," Journal of Pharmacy and Pharmacology, Jan. 1, 1994, vol. 46, No. 1, pp. 23-28.

Zlokovic et al., "Evidence for Transcapillary Transport of Reduced Glutathione in Vascular Perfused Guinea-Pig Brain," Biochemical and Biophysical Research Communications, May 30, 1994, vol. 201, No. 1, pp. 402-408.

Zlokovic, "Cerebrovascular Permeability to Peptides: Manipulations of Transport Systems at the Blood-Brain Barrier," Pharmaceutical Research, 1995, vol. 12, No. 10, pp. 1395-1406.

"How many mental illnesses are there?" Medical News Today, 2004, http://www.medicalnewstoday.com/releases/9671.php.

USPTO Office Action for U.S. Appl. No. 12/721,633 dated Feb. 25, 2013.

Walsh, S. et al, "Inflammatory processes and Alzheimer's disease," Expert. Rev. Neurotherapeutics, 2004, vol. 4., No. 5, pp. 793-798.

USPTO Office Action for U.S. Appl. No. 12/721,633 dated Oct. 26, 2012.

Japanese Office Action (Notice of Allowance) for Japanese Application No. 2010-007125, dated Oct. 8, 2013.

* cited by examiner

GLUTATHIONE-BASED DELIVERY SYSTEM

This application is a Divisional of U.S. patent application Ser. No. 12/244,563, filed Oct. 2, 2008, now U.S. Pat. No. 8,067,380 which is a Continuation-In-Part of U.S. patent application Ser. No. 12/000,261, filed Dec. 11, 2007, now U.S. Pat. No. 7,704,956 which issued Apr. 27, 2010. Application Ser. No. 12/000,261 is a Continuation-In-Part of U.S. patent application Ser. No. 11/303,934, filed Dec. 19, 2005, now U.S. Pat. No. 7,446,096, which issued on Nov. 4, 2008. This application also claims priority under 35 U.S.C. §119(a) of Taiwan Patent Application No. 94147661, filed on Dec. 30, 2005. The entire contents of each of the above-identified applications are hereby incorporated by reference.

BACKGROUND OF THE INVENTION

1. Field of the Invention

The invention relates to a biological delivery system, and more particularly to a glutathione-based delivery system.

2. Description of the Related Art

The blood brain barrier (BBB) is composed of brain endothelial cells capable of blocking foreign substances, such as toxin, due to the tight junction therebetween. Hydrophobic or low-molecular-weight molecules, however, can pass through the BBB via passive diffusion.

Nevertheless, active compounds, such as hydrophilic protein drugs for treating cerebral or nervous diseases and analgesic peptide drugs acting on the central nervous system, cannot enter brain tissue thereby due to their large molecular weight or hydrophilicity, resulting in decomposition by enzymes.

Current researches forward various methods of allowing active compounds to pass through the BBB, including structural modification to increase hydrophobicity of drugs, absorption-mediated transport (AMT) allowing positive-charged carriers to pass via charge absorption, carrier-mediated transcytosis (CMT) allowing hydrophilic metal ions such as $Na^+$ and $K^+$, di-peptides, tri-peptides or glucose to pass via transporters, and receptor-mediated transcytosis (RMT) allowing macro molecules such as insulin, transferrin, or low-density lipoprotein (LDL) to pass via transcytosis.

Glutathione (GSH) is an endogenous antioxidant. If its concentration in serum is insufficient, some nervous diseases, such as chronic fatigue syndrome (CFS), may occur.

In 1988, Kiwada Hiroshi provided a liposome capable of accumulation in liver comprising an N-acylglutathione such as N-palmitoylglutathione and a phospholipid such as phosphotidylcholine to target and treat liver diseases recited in JP63002922.

In 1994, Berislav V. Zlokovic asserted that glutathione (GSH) reaches and passes through the BBB of a guinea pig via a special route, such as GSH-transporter, without decomposition.

In 1995, Berislav V. Zlokovic asserted that glutathione (GSH) exists in brain astrocyte and endothelial cells with millimolar concentration.

In 1995, Ram Kannan asserted that GSH uptake depends on $Na^+$ concentration. If $Na^+$ concentration is low, GSH uptake from brain endothelial cells may be inhibited. He also pointed Na-dependent GSH transporter located on the luminal side of the BBB manages GSH uptake and Na-independent GSH transporter located on the luminal side of the BBB manages efflux of GSH. Additionally, Kannan built a rat hepatic canalicular GSH transporter (RcGSHT) system using the brains of mice and guinea pigs to analyze cDNA fragments 5, 7, and 11. The results indicate that fragment 7 represents Na-dependent GSH transporter and fragments 5 and 11 represent Na-dependent GSH transporter.

In 1999, Ram Kannan built a mouse brain endothelial cell line (MBEC-4) model simulating BBB situations. The model proved that Na-dependent GSH transporter is located on the luminal side of the MBEC-4 cell.

In 2000, Ram Kannan asserted that GSH passes through the BBB via Na-dependent GSH transporter in human cerebrovascular endothelial cells (HCEC) and Na-dependent GSH transporter exists in the luminal plasma membrane of HCEC.

In 2003, Zhao Zhiyang provided an anti-cancer pro-drug bonded with glutathione s-transferase (GST)/glutathione (GSH) by sulfonamide covalent bonds to target and treat specific cancer cells after broken of the sulfonamide bonds recited in US2003109555. This modification can protect amino groups of drugs, increase solubility thereof, and alter absorption and distribution thereof in body.

BRIEF SUMMARY OF THE INVENTION

One embodiment of the invention provides a delivery system comprising a carrier or an active compound, and a glutathione ligand or a glutathione derivative ligand, wherein the glutathione ligand or the glutathione derivative ligand is covalently bound to the carrier or the active compound, and the glutathione ligand or the glutathione derivative ligand is on an outside surface of the carrier.

One embodiment of the invention provides a compound comprising a moiety comprising a vitamin E, a vitamin E derivative or a phospholipid, a polyethylene glycol or a polyethylene glycol derivative covalently bound thereto, and a glutathione or a glutathione derivative covalently bound to the polyethylene glycol or the polyethylene glycol derivative.

A detailed description is given in the following embodiments with reference to the accompanying drawings.

BRIEF DESCRIPTION OF THE DRAWINGS

The invention can be more fully understood by reading the subsequent detailed description and examples with references made to the accompanying drawing, wherein.

DETAILED DESCRIPTION OF THE INVENTION

Figure 1:
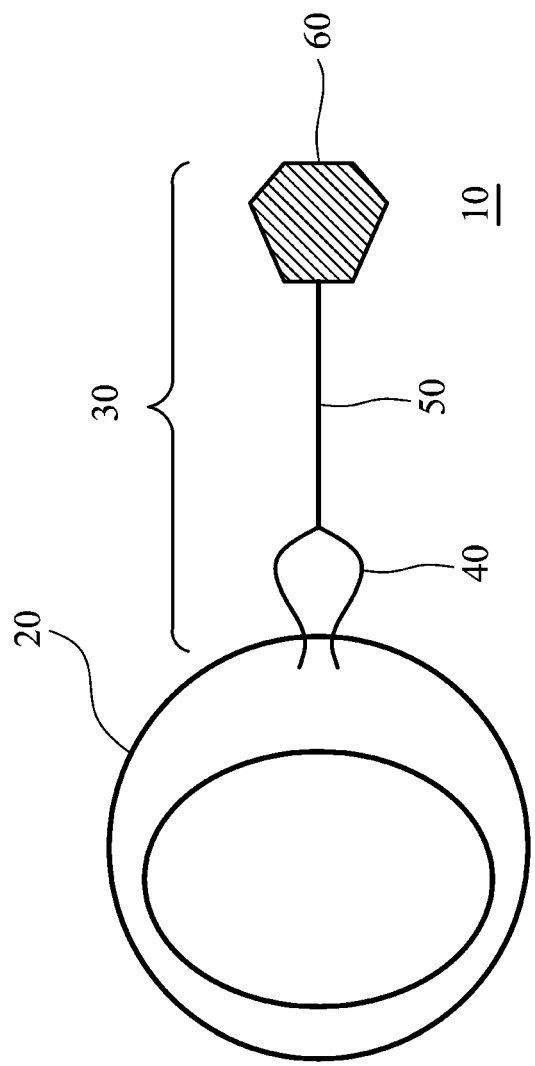
FIG. 1 shows a delivery system of the invention.

The following description is of the best-contemplated mode of carrying out the invention. This description is made for the purpose of illustrating the general principles of the invention and should not be taken in a limiting sense. The scope of the invention is best determined by reference to the appended claims.

One embodiment of the invention provides a delivery system comprising a carrier or an active compound, and a glutathione ligand or a glutathione derivative ligand. The glutathione ligand or the glutathione derivative ligand is covalently bound to the carrier or the active compound. The glutathione ligand or the glutathione derivative ligand is on an outside surface of the carrier.

The carrier may comprise a nanoparticle, a polymeric nanoparticle, a solid liquid nanoparticle, a polymeric micelle, a liposome, microemulsion, or a liquid-based nanoparticle. The liposome may comprise at least one of lecithin such as soy lecithin and hydrogenated lecithin such as hydrogenated soy lecithin.

The liposome may further comprise cholesterol, water-soluble vitamin E, or octadecyl amine to increase serum resistance or charge amounts. The molar composition ratio of the liposome may be 0.5-100% of lecithin or hydrogenated lecithin, 0.005-75% of cholesterol or water-soluble vitamin E, and 0.001-25% of octadecyl amine.

The carrier may further encapsulate an active compound with an encapsulation efficiency of about 0.5-100%. The active compound may comprise small molecule compounds such as gabapentin, peptides such as enkephalin, proteins, DNA plasmids, oligonucleotides, or gene fragments and have a molar ratio of about 0.0005-50% in the carrier.

The sulfhydryl group (—SH) of the glutathione ligand may be modified to form the glutathione derivative ligand. The glutathione derivative ligand may have formula (III).

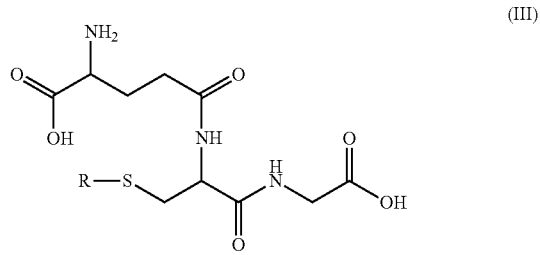
(III)

In formula (III), the original sulfhydryl group (—SH) of the glutathione ligand is replaced by —SR. R may comprise C1-10 alkyl or lactoyl (—CO—CH(OH)—CH3).

The glutathione derivative ligand may have formula (IV).

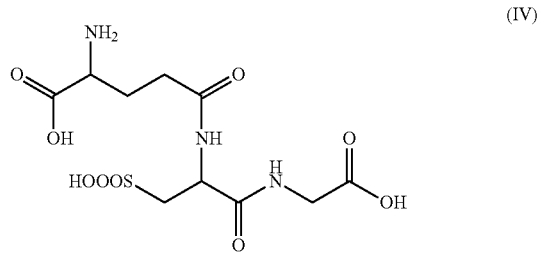
(IV)

In formula (IV), the original sulfhydryl group (—SH) of the glutathione ligand is replaced by sulfonic acid (—SOOOH).

The carrier or the active compound may target glutathione transporters of organs such as a heart, lung, liver, kidney, or blood brain barrier (BBB).

Specifically, the active compound may pass through the blood brain barrier, such as brain endothelial cells, with a cell penetration rate of about 0.01-100%.

One embodiment of the invention provides a compound comprising a moiety comprising a vitamin E, a vitamin E derivative or a phospholipid, a polyethylene glycol or a polyethylene glycol derivative covalently bound thereto, and a glutathione or a glutathione derivative covalently bound to the polyethylene glycol or the polyethylene glycol derivative.

The vitamin E derivative may comprise tocopherol derivatives or tocotrienol derivatives and may be α-tocopherol, β-tocopherol, γ-tocopherol, δ-tocopherol, α-tocotrienol, β-tocotrienol, γ-tocotrienol, δ-tocotrienol, α-tocopherol succinate, β-tocopherol succinate, γ-tocopherol succinate, δ-tocopherol succinate, α-tocotrienol succinate, β-tocotrienol succinate, γ-tocotrienol succinate, δ-tocotrienol succinate, α-tocopherol acetate, β-tocopherol acetate, γ-tocopherol acetate, δ-tocopherol acetate, α-tocotrienol acetate, β-tocotrienol acetate, γ-tocotrienol acetate, δ-tocotrienol acetate, α-tocopherol nicotinate, β-tocopherol nicotinate, γ-tocopherol nicotinate, δ-tocopherol nicotinate, α-tocotrienol nicotinate, β-tocotrienol nicotinate, γ-tocotrienol nicotinate, δ-tocotrienol nicotinate, α-tocopherol phosphate, β-tocopherol phosphate, γ-tocopherol phosphate, δ-tocopherol phosphate, α-tocotrienol phosphate, β-tocotrienol phosphate, γ-tocotrienol phosphate, or δ-tocotrienol phosphate.

The phospholipid may have formulae (I) or (II).

(I)

or

(II)

In formula (I), $A_1$ may be sphingosine and $R_1$ may comprise octanoyl or palmitoyl. In formula (II), $A_2$ may be phosphoethanoamine and $R_2$ may comprise myristoyl, palmitoyl, stearoyl, or oleoyl.

The polyethylene glycol or the polyethylene glycol derivative may have a polymerization number (n) of about 6-210. The molecular weight of the polyethylene glycol or the polyethylene glycol derivative may be altered with various vitamin E derivatives or phospholipids. For example, when PEG or its derivative is bound to vitamin E derivatives, it may have a molecular weight of about 300-10,000, when PEG or its derivative is bound to the phospholipid represented by formula (I), it may have a molecular weight of about 750-5,000, and when PEG or its derivative is bound to the phospholipid represented by formula (II), it may have a molecular weight of about 350-5,000.

The polyethylene glycol derivative may comprise carboxylic acid, maleimide, PDP, amide, or biotin.

The sulfhydryl group (—SH) of the glutathione may be modified to form the glutathione derivative. The glutathione derivative may have formula (III).

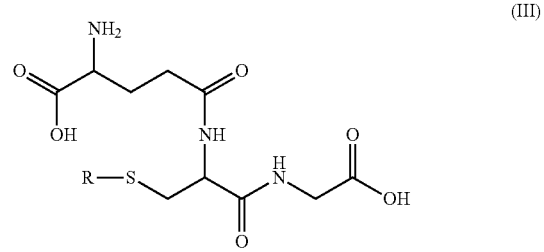
(III)

In formula (III), the original sulfhydryl group (—SH) of the glutathione is replaced by —SR. R may comprise C1-10 alkyl or lactoyl (—CO—CH(OH)—CH3).

The glutathione derivative may have formula (IV).

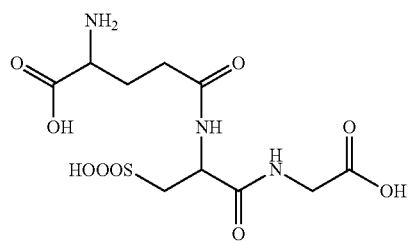

(IV)

In formula (IV), the original sulfhydryl group (—SH) of the glutathione is replaced by sulfonic acid (—SOOOH).

Referring to FIG. 1, a delivery system of the invention is illustrated. The delivery system 10 comprises a carrier 20 and a ligand 30 bound thereto. The ligand 30 comprises a moiety 40 comprising a vitamin E, a vitamin E derivative or a phospholipid, a polyethylene glycol or a polyethylene glycol derivative 50 bound thereto, and a glutathione or a glutathione derivative 60 bound to the polyethylene glycol and the polyethylene glycol derivative.

Active compounds, such as proteins, peptides, or small molecules, transported by the targeted carrier with a novel glutathione ligand provided by the invention can effectively pass through blood brain barrier by carrier-mediated transcytosis (CMT) or receptor-mediated transcytosis (RMT) to treat cerebral or nervous diseases.

EXAMPLE 1

Preparation of TPGS-Glutathione

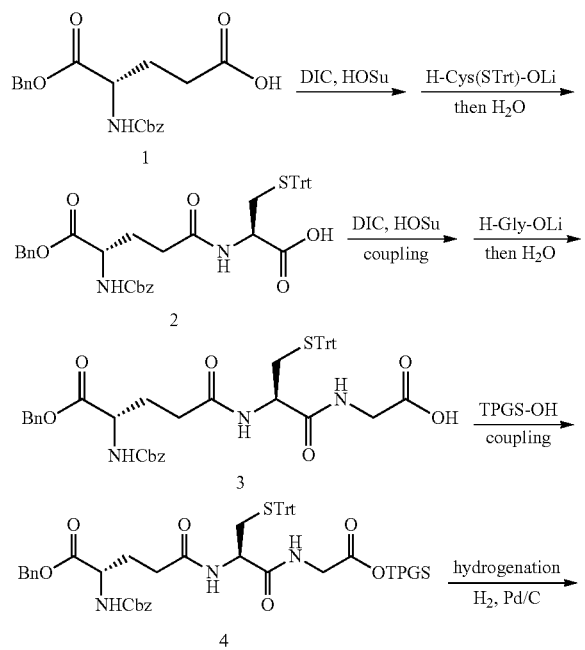

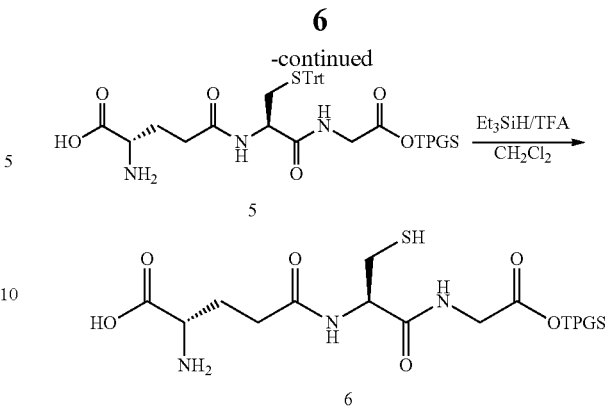

A stirred solution of N-Cbz Benzyl amino acid (N-Cbz Glutamine, 1.0 equiv) and N-hydroxysuccinimide (HOSu, 1.0 equiv) in DME (15 mL) was cooled to 0° C. Dicyclohexylcarbodiimide (DIC, 1.0 equiv) was added and stirred at this temperature for 4 hr. The reaction mixture was allowed to stand for 2 hr in a refrigerator and then filtered.

As expected, the pure compound was obtained in excellent yield (98%) after filtration of the dicyclohexylurea (DCU) formed and evaporation of the solvent. The residue was triturated in Et$_2$O/hexanes, filtered out, and then dried in vacuo to afford a white solid.

The (+)-S-tritylcysteine lithium salt (H-Cys(STrt)-OLi, 1.0 equiv) and sodium carbonate (Na$_2$CO$_3$, 5.0 equiv) were dissolved in water (15 mL), and then acetonitrile (CH$_3$CN) was added followed by the intermediated product obtained in Step-2. The mixture was vigorously stirred at room temperature for 3-6 hr until the TLC analysis indicated the absence of intermediated product in Step-2. The solution was washed with water (2*100 mL) and the organic phase was dried with Na$_2$SO4, filtered, and concentrated in vacuo to afford the compound 2.

A stirred solution of compound 2 and N-hydroxysuccinimide (HOSu, 1.0 equiv) in DME (15 mL) was cooled to 0° C. Dicyclohexylcarbodiimide (DIC, 1.0 equiv) was added and stirred at this temperature for 4 hr. The reaction mixture was allowed to stand for 2 hr in a refrigerator and then filtered.

After the DCU and solvent was removed, the glycine lithium salt (H-Gly-OLi, 1.0 equiv) and sodium carbonate (Na$_2$CO$_3$, 5.0 equiv) were dissolved in water (15 mL), and then acetonitrile (CH$_3$CN) was added followed by the intermediated product obtained in Step-4. The mixture was vigorously stirred at room temperature for 3-6 hr until the TLC analysis indicated the absence of intermediated product in Step-4. The solution was washed with water (2*100 mL) and the organic phase was dried with Na$_2$SO$_4$, filtered, and concentrated in vacuo to afford the compound 3.

The d-alpha tocopheryl polyethylene glycol 1000 succinate (TPGS-OH) was coupling with compound 3 via esterification to afford the compound 4.

The compound 4 in methanol (100 mL) was added 10% Pd—C (0.2 times the weight of protected tripeptide-TPGS). The suspension was stirred at room temperature for 16 hr under a balloon filled with hydrogen. The suspension was filtered through Celite and evaporated, and the residue was crystallized from ethanol. Then, the compound 5 was obtained.

Triethylsilane (Et$_3$SiH) and TFA-mediated deprotection of compound 5 in the presence of CH$_2$Cl$_2$ provided the compound 6 (that is GSH-TPGS).

The preparation of TPGS-Glutathione derivatives is similar to the foregoing processes. The distinctions therebetween are simply further modifications of the sulfhydryl group (—SH) of the TPGS-Glutathione. For example, modifications may be performed, by substitutable groups such as C1-12 alkyl or lactoyl (—CO—CH(OH)—CH3), or oxidization to form sulfonic acid (—SOOOH). The Glutathione and its derivatives are covalently bound to the TPGS with an ester bond.

Preparation of Met-Enkephalin Carrier Solution 0.5 g lipid containing 83.2% soybean phosphatidylcholine (SPC), 4.2% α-tocopherol succinate PEG 1500 (TPGS), 4.2% glutathione-TPGS (GSH-TPGS), and 8.4% cholesterol was placed in a 12.5 mL $ZrO_2$ mortar. Appropriate amounts of met-enkephalin were dissolved in 10 mM phosphate solution with pH 7.4 to form a 4% drug solution. 0.5 mL drug solution and five $ZrO_2$ beads (10 mm of diameter) were then added to the mortar and ground with 500 rpm for one hour to form a sticky cream. Next, 0.2 g sticky cream and 1.8 mL phosphate solution (10 mM, pH 7.4) were added to a 10 mL flask to hydrate under room temperature for one hour to form a carrier solution containing liposomes encapsulating met-enkephalin. The concentration of met-enkephalin in a liposome was 0.56 mg/mL. The encapsulation efficiency thereof was 33.3%. The mean diameter of the carrier was 173.1 nm as well as the polydispersity index (PI) was 0.243.

EXAMPLES 2-6

Preparation methods of Examples 2-6 are similar to Example 1. The distinctions therebetween are the various carrier compositions. Please see Tables 1 and 2.

TABLE 1

| Examples | Soy lecithin | H-soy lecithin | Cholesterol | TPGS | TPGS-GSH | Octadecyl amine | Met-enkephalin |
|---|---|---|---|---|---|---|---|
| 2 | 10 | — | 1 | — | 1 | — | 0.48 |
| 3 | 10 | — | 1 | — | 1 | 1 | 1.60 |
| 4 | 9 | 1 | 1 | 0.5 | 0.5 | — | 1.60 |
| 5 | 9 | 1 | 1 | 0.75 | 0.25 | — | 1.60 |
| 6 | 9 | 1 | 1 | — | 1 | — | 1.60 |

TABLE 2

| Examples | Mean diameter (nm) | PI | Met-enkephalin concentration (mg/mL) | Encapsulation efficiency (%) |
|---|---|---|---|---|
| 2 | 162.7 | 0.227 | 0.56 | 31.70 |
| 3 | 161.4 | 0.046 | 4.00 | 70.33 |
| 4 | 214.1 | 0.003 | 3.25 | 68.85 |
| 5 | 165.3 | 0.137 | 3.40 | 68.48 |
| 6 | 214.5 | 0.116 | 3.99 | 80.78 |

EXAMPLE 7

Preparation of Gabapentin Carrier Solution 0.5 g lipid containing 83.2% soybean phosphatidylcholine (SPC), 4.2% α-tocopherol succinate PEG 1500 (TPGS), 4.2% glutathione-TPGS (GSH-TPGS), and 8.4% cholesterol was placed in a 12.5 mL $ZrO_2$ mortar. Appropriate amounts of gabapentin were dissolved in 10 mM phosphate solution with pH 7.4 to form a 10% drug solution. 0.5 mL drug solution and five $ZrO_2$ beads (10 mm of diameter) were then added to the mortar and ground with 500 rpm for one hour to form a sticky cream. Next, 0.2 g sticky cream and 1.8 mL phosphate solution (10 mM, pH 7.4) were added to a 10 mL flask to hydrate under room temperature for one hour to form a carrier solution containing liposomes encapsulating gabapentin. The concentration of gabapentin in a liposome was 1.08 mg/mL. The encapsulation efficiency thereof was 35.7%. The mean diameter of the carrier was 147.7 nm as well as the polydispersity index (PI) was 0.157.

COMPARATIVE EXAMPLE 1

Preparation of Met-Enkephalin Carrier Solution 0.5 g lipid containing 83.2% soybean phosphatidylcholine (SPC), 8.4% α-tocopherol succinate PEG 1500 (TPGS), and 8.4% cholesterol was placed in a 12.5 mL $ZrO_2$ mortar. Appropriate amounts of met-enkephalin were dissolved in 10 mM phosphate solution with pH 7.4 to form a 4% drug solution. 0.5 mL drug solution and five $ZrO_2$ beads (10 mm of diameter) were then added to the mortar and ground with 500 rpm for one hour to form a sticky cream. Next, 0.2 g sticky cream and 1.8 mL phosphate solution (10 mM, pH 7.4) were added to a 10 mL flask to hydrate under room temperature for one hour to form a carrier solution containing liposomes encapsulating met-enkephalin. The concentration of met-enkephalin in a liposome was 0.57 mg/mL. The encapsulation efficiency thereof was 31.1%. The mean diameter of the carrier was 164.1 nm as well as the polydispersity index (PI) was 0.281.

COMPARATIVE EXAMPLES 2-3

Preparation methods of Comparative Examples 2-3 are similar to Comparative Example 1. The distinctions therebetween are the various carrier compositions. Please see Tables 3 and 4.

TABLE 3

| Comparative Examples | Soy lecithin | H-soy lecithin | Cholesterol | TPGS | Octadecyl amine | Met-enkephalin |
|---|---|---|---|---|---|---|
| 2 | 10 | — | 1 | 1 | 1 | 1.60 |
| 3 | 9 | 1 | 1 | 1 | — | 1.60 |

TABLE 4

| Comparative Examples | Mean diameter (nm) | PI | Met-enkephalin concentration (mg/ml) | Encapsulation efficiency (%) |
|---|---|---|---|---|
| 2 | 159.7 | 0.103 | 3.58 | 70.17 |
| 3 | 149.0 | 0.168 | 3.22 | 69.67 |

COMPARATIVE EXAMPLE 4

Preparation of Gabapentin Carrier Solution 0.5 g lipid containing 83.2% soybean phosphatidylcholine (SPC), 8.4% α-tocopherol succinate PEG 1500 (TPGS), and 8.4% cholesterol was placed in a 12.5 mL $ZrO_2$ mortar. Appropriate amounts of gabapentin were dissolved in 10 mM phosphate solution with pH 7.4 to form a 10% drug solution. 0.5 mL drug solution and five $ZrO_2$ beads (10 mm of diameter) were then added to the mortar and ground with 500 rpm for one hour to form a sticky cream. Next, 0.2 g sticky cream and 1.8 mL phosphate solution (10 mM, pH 7.4) were added to a 10 mL flask to hydrate under room temperature for one hour to form a carrier solution containing liposomes encapsulating gabapentin. The concentration of gabapentin in a liposome was 1.17 mg/mL. The encapsulation efficiency thereof was 38.5%. The mean diameter of the carrier was 155.8 nm as well as the polydispersity index (PI) was 0.186.

EXAMPLE 8

In Vitro Penetration Rate Test 1 of Met-Enkephalin Liposome

The penetration rate of met-enkephalin was measured using a RBE4/glioma cell model simulating BBB situations. The test results of Examples 1-2 (containing glutathione) and Comparative Example 1 (without glutathione) are compared in Table 5.

TABLE 5

| Examples | Drug dose (µg) | Penetration rate (%) | SD |
|---|---|---|---|
| Comparative Example 1 | 182.6 | 3.4 | 0.6 |
| Example 1 | 167.7 | 9.8 | 1.3 |
| Example 2 | 165.2 | 9.8 | 1.2 |

The results indicate that Examples 1 and 2 have an apparently higher penetration rate (9.8%) of about 2.82 times greater than Comparative Example 1 (3.4%).

EXAMPLE 9

In Vitro Penetration Rate Test 2 of Met-Enkephalin Liposome

The penetration rate of met-enkephalin was measured using a RBE4/glioma cell model simulating BBB situations. The test results of Example 3 (containing glutathione) and Comparative Example 2 (without glutathione) are compared in Table 6.

TABLE 6

| Examples | Drug dose (µg) | Penetration rate (%) | SD |
|---|---|---|---|
| Comparative Example 2 | 250.0 | 3.55 | 0.36 |
| Example 3 | 250.0 | 6.99 | 1.43 |
| Example 3 (glutathione added) | 250.0 | 0.25 | 0.03 |

The results indicate that Example 3 has an apparently higher penetration rate (6.99%) of about 1.96 times greater than Comparative Example 2 (3.55%). Additionally, if cells were cultured with glutathione for 30 min before Example 3 was performed, the penetration rate thereof was lowered by 0.25% due to the addition of glutathione which occupied the glutathione transporter of the cells to block binding of carriers, reducing drug penetration through the BBB. The result proves that the glutathione carrier provided by the invention passes through the BBB via glutathione ligand/transporter binding to induce carrier-mediated transcytosis (CMT) or receptor-mediated transcytosis (RMT).

EXAMPLE 10

Hot-Plate Test of Met-Enkephalin Liposome

Figure 2:
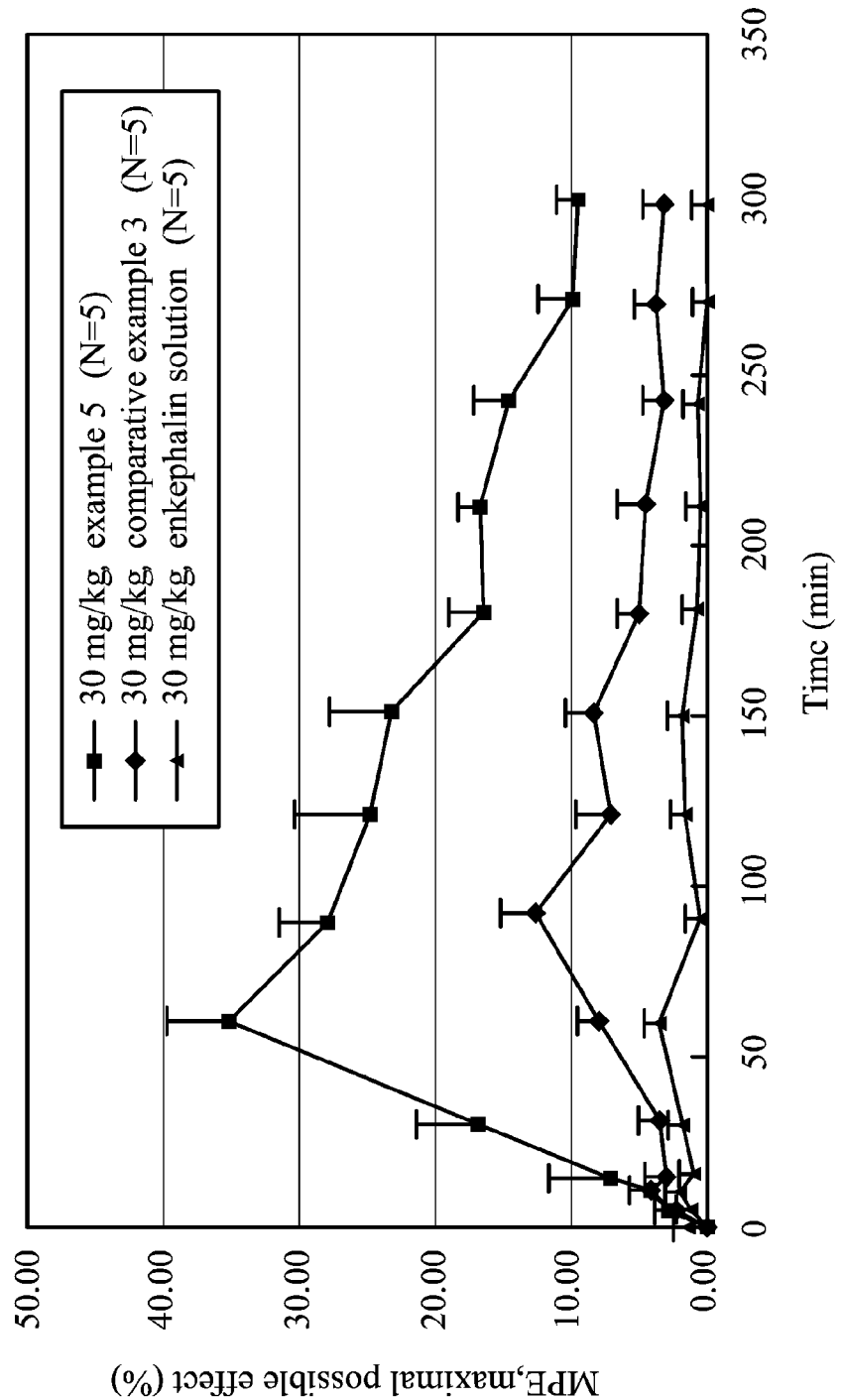
FIG. 2 shows maximal possible effect (MPE) of various met-enkephalin carriers of the invention.
Figure 3:
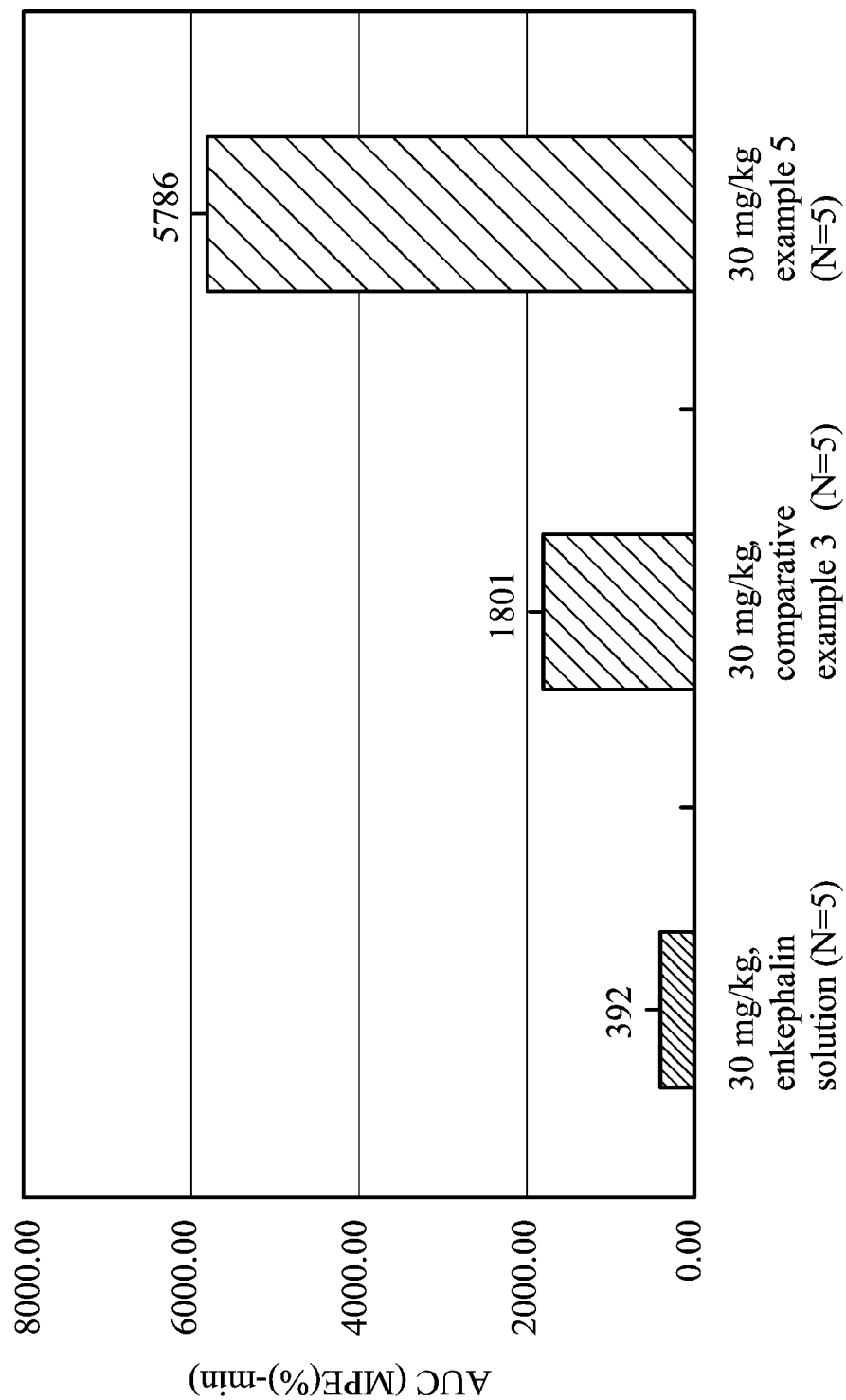
FIG. 3 shows area under curve (AUC) of various met-enkephalin carriers of the invention.

After a laboratory mouse on a 55° C. hot plate was intravenously injected, the analgesic effect on heat-induced pain was evaluated. Referring to FIG. 2, for carriers without glutathione (Comparative Example 3), 90 min after injection, the maximal possible effect (MPE) of a 30 mg/mL dose was 13%. For carriers containing glutathione (Example 5), 60 min after injection, the maximal possible effect (MPE) of 30 mg/mL dose was 37%. Referring to FIG. 3, according to the area under curve (AUC), Example 5 provides 3.2 times the analgesic effect of Comparative Example 3 and 14.7 times the met-enkephalin solution. Thus, drugs can be safely carried by the carrier with glutathione ligand to pass through the BBB to achieve analgesic effect.

EXAMPLE 11

Hot-Plate Test of Gabapentin Liposome

Figure 4:
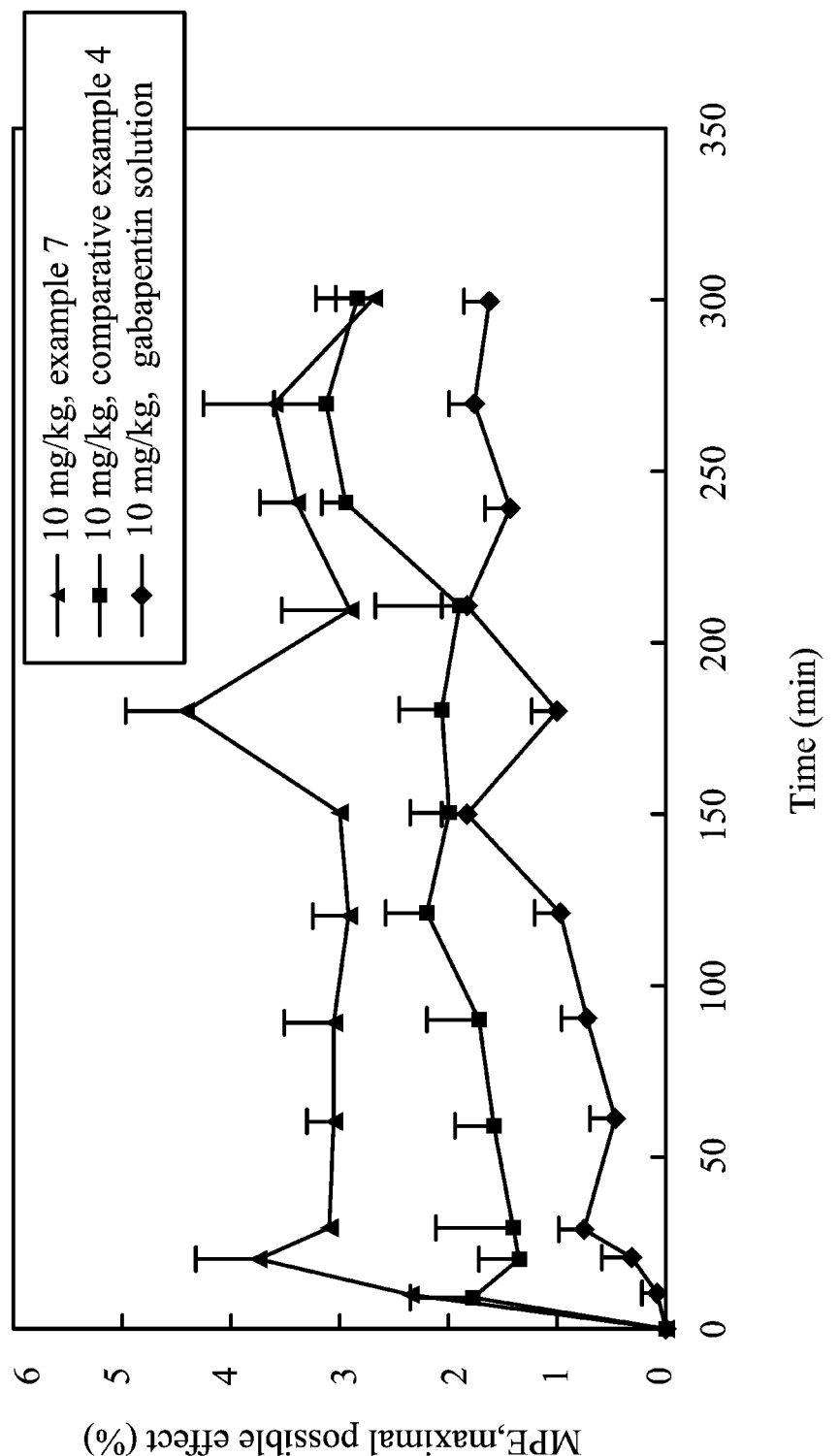
FIG. 4 shows maximal possible effect (MPE) of various gabapentin carriers of the invention.
Figure 5:
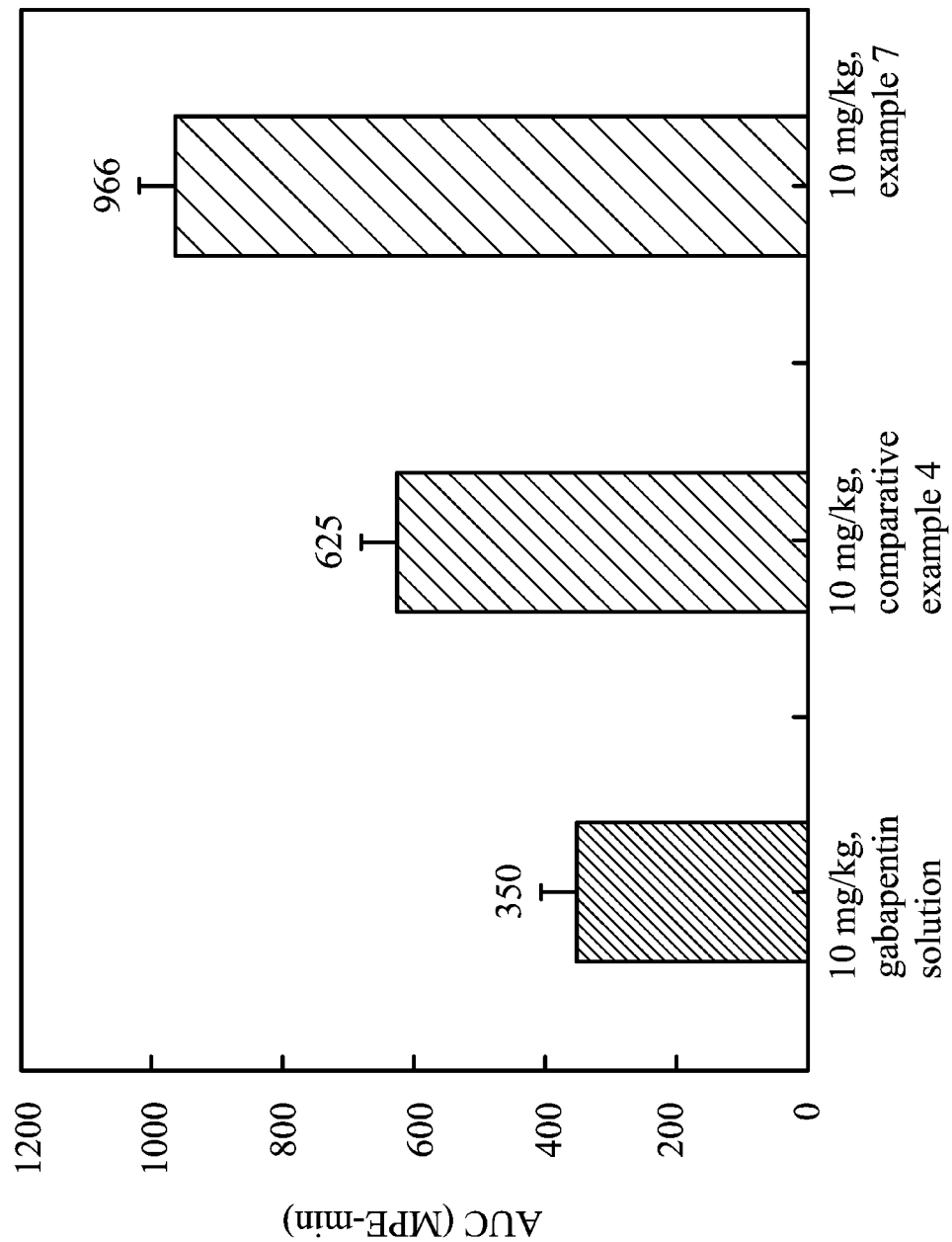
FIG. 5 shows area under curve (AUC) of various gabapentin carriers of the invention.

After a laboratory mouse on a 55° C. hot plate was intravenously injected, the analgesic effect on heat-induced pain was evaluated. Referring to FIG. 4, for carriers without glutathione (Comparative Example 4), 270 min after injection, the maximal possible effect (MPE) of a 10 mg/mL dose was 3.15%. For carriers containing glutathione (Example 7), 180 min after injection, the maximal possible effect (MPE) of a 10 mg/mL dose was 4.47%. Referring to FIG. 5, according to the area under curve (AUC), Example 7 provides 1.54 times the analgesic effect of Comparative Example 4 ($p<0.005$) and 2.76 times the gabapentin solution ($p<0.0005$). Thus, drugs can be safely carried by the carrier with glutathione ligand to pass through the BBB to achieve analgesic effect.

EXAMPLE 12

Serum Stability Test of Met-Enkephalin Liposome

Figure 6:
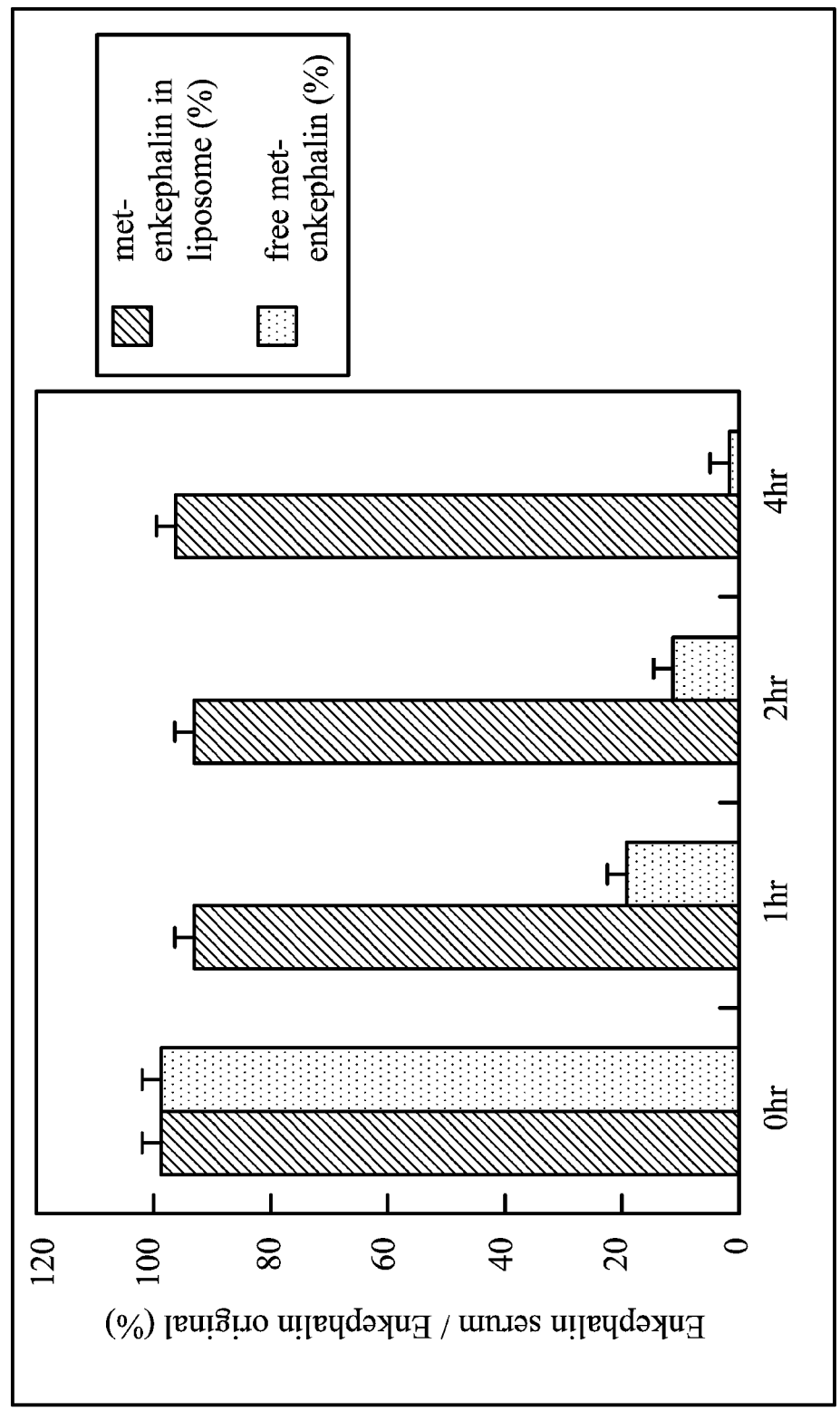
FIG. 6 shows serum stability of free met-enkephalin and met-enkephalin in liposomes.

The carriers provided by Example 5 and fetal bovine serum (FBS) were mixed with 1:1 (v/v) to form a solution. After being placed in a 37° C. water bath for 0, 1, 2, and 4 hours, respectively, the solution was analyzed by gel filtration (Sephrox CL-4B, 75 mm×120 mm) and measured residual concentration of met-enkephalin in liposomes. The results are shown in FIG. 6.

The results indicate that the concentration of met-enkephalin in liposomes remains 93% above. However, residual concentration of free met-enkephalin decreases to 2%. It is clear that the carrier provided by the invention has high serum resistance.

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A compound, comprising:
   a first moiety comprising a vitamin E, a vitamin E derivative or a phospholipid;
   a second moiety comprising a polyethylene glycol or a polyethylene glycol derivative covalently bound to the first moiety; and
   a third moiety comprising a glutathione or a glutathione derivative covalently bound to the second moiety.

2. The compound as claimed in claim 1, wherein the vitamin E derivative comprises tocopherol derivatives or tocotrienol derivatives.

3. The compound as claimed in claim 1, wherein the vitamin E derivative comprises α-tocopherol, β-tocopherol, γ-tocopherol, δ-tocopherol, α-tocotrienol, β-tocotrienol, γ-tocotrienol, δ-tocotrienol, α-tocopherol succinate, β-tocopherol succinate, γ-tocopherol succinate, δ-tocopherol succinate, α-tocotrienol succinate, β-tocotrienol succinate, γ-tocotrienol succinate, δ-tocotrienol succinate, α-tocopherol acetate, β-tocopherol acetate, γ-tocopherol acetate, δ-tocopherol acetate, α-tocotrienol acetate, β-tocotrienol acetate, γ-tocotrienol acetate, δ-tocotrienol acetate, α-tocopherol nicotinate, β-tocopherol nicotinate, γ-tocopherol nicotinate, δ-tocopherol nicotinate, α-tocotrienol nicotinate, β-tocotrienol nicotinate, γ-tocotrienol nicotinate, δ-tocotrienol nicotinate, α-tocopherol phosphate, β-tocopherol phosphate, γ-tocopherol phosphate, δ-tocopherol phosphate, α-tocotrienol phosphate, β-tocotrienol phosphate, γ-tocotrienol phosphate, or δ-tocotrienol phosphate.

4. The compound as claimed in claim 1, wherein the phospholipid has formula (I):

$$R_1\text{-}A_1\text{-} \quad (I)$$

wherein $A_1$ is sphingosine and $R_1$ comprises octanoyl or palmitoyl.

5. The compound as claimed in claim 1, wherein the phospholipid has formula (II):

wherein $A_2$ is phosphoethanoamine and $R_2$ comprises myristoyl, palmitoyl, stearoyl, or oleoyl.

6. The compound as claimed in claim 1, wherein the polyethylene glycol or the polyethylene glycol derivative has a polymerization number (n) of about 6-210.

7. The compound as claimed in claim 1, wherein when the first moiety is the vitamin E derivative, the polyethylene glycol or the polyethylene glycol derivative has a molecular weight of about 300-10,000.

8. The compound as claimed in claim 4, wherein the polyethylene glycol or the polyethylene glycol derivative has a molecular weight of about 750-5,000.

9. The compound as claimed in claim 5, wherein the polyethylene glycol or the polyethylene glycol derivative has a molecular weight of about 350-5,000.

10. The compound as claimed in claim 1, wherein the polyethylene glycol derivative comprises carboxylic acid, maleimide, PDP, amide, or biotin.

* * * * *